(12) United States Patent
McKay

(10) Patent No.: US 9,949,832 B2
(45) Date of Patent: Apr. 24, 2018

(54) OSTEOGRAFT IMPLANT

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/048,170

(22) Filed: Feb. 19, 2016

(65) Prior Publication Data

US 2016/0166385 A1  Jun. 16, 2016

Related U.S. Application Data

(62) Division of application No. 13/736,490, filed on Jan. 8, 2013, now Pat. No. 9,265,609.

(51) Int. Cl.
| | |
|---|---|
| *A61F 2/28* | (2006.01) |
| *A61L 27/36* | (2006.01) |
| *A61L 27/50* | (2006.01) |
| *A61F 2/30* | (2006.01) |

(52) U.S. Cl.
CPC ............ *A61F 2/28* (2013.01); *A61L 27/3608* (2013.01); *A61L 27/50* (2013.01); *A61F 2002/2835* (2013.01); *A61F 2002/2839* (2013.01); *A61F 2002/30059* (2013.01); *A61F 2002/30261* (2013.01); *A61F 2230/0069* (2013.01); *A61F 2310/00179* (2013.01); *A61F 2310/00359* (2013.01); *A61F 2310/00371* (2013.01); *A61L 2430/02* (2013.01)

(58) Field of Classification Search
CPC ...... A61F 2/28; A61F 2/00; A61F 2/44; A61F 13/00
USPC .......... 623/16.11, 17.11–17.19, 23.47–23.63; 523/113–116; 424/422–426
See application file for complete search history.

(56) References Cited

U.S. PATENT DOCUMENTS

| | | |
|---|---|---|
| 5,112,354 A | 5/1992 | Sires |
| 5,899,939 A | 5/1999 | Boyce et al. |
| 6,090,998 A | 7/2000 | Grooms et al. |
| 6,123,731 A | 9/2000 | Boyce et al. |
| 6,143,033 A | 11/2000 | Paul et al. |
| 6,162,225 A | 12/2000 | Gertzman et al. |
| 6,206,923 B1 | 3/2001 | Boyd et al. |
| 6,290,718 B1 | 9/2001 | Grooms et al. |
| D450,121 S | 11/2001 | Anderson |
| 6,340,477 B1 | 1/2002 | Anderson |
| D458,373 S | 6/2002 | Jackson |
| 6,409,765 B1 | 6/2002 | Bianchi et al. |
| 6,440,444 B2 | 8/2002 | Boycem et al. |

(Continued)

FOREIGN PATENT DOCUMENTS

| | | |
|---|---|---|
| WO | 1996039203 A1 | 12/1996 |
| WO | 2000035511 A1 | 6/2000 |
| WO | 2001008714 A1 | 2/2001 |

*Primary Examiner* — Yashita Sharma

(57) ABSTRACT

Bone implant compositions are provided that include a body made of cortical bone extending along an axis between a first end and a second end. The body includes an outer surface configured to engage host bone of a patient and at least one recess extending transverse to the axis into the outer surface of the body configured for disposal of an insert. At least one insert made of demineralized bone is disposed in the at least one recess.

2 Claims, 10 Drawing Sheets

(56) References Cited

U.S. PATENT DOCUMENTS

| | | |
|---|---|---|
| 6,454,811 B1 | 9/2002 | Sherwood et al. |
| 6,458,375 B1 | 10/2002 | Gertzman et al. |
| D467,341 S | 12/2002 | Meyer et al. |
| 6,530,955 B2 | 3/2003 | Boyle et al. |
| 6,547,823 B2 | 4/2003 | Scarborough et al. |
| 6,599,520 B2 | 7/2003 | Scarborough et al. |
| 6,616,698 B2 | 9/2003 | Scarborough |
| 6,730,124 B2 | 5/2004 | Steiner |
| 6,761,739 B2 | 7/2004 | Shepard |
| 6,827,720 B2 | 12/2004 | Leali |
| 6,855,167 B2 | 2/2005 | Shimp et al. |
| 6,902,578 B1 | 6/2005 | Anderson et al. |
| 7,001,551 B2 | 2/2006 | Meredith |
| 7,044,968 B1 | 5/2006 | Yaccarino, III et al. |
| 7,115,146 B2 * | 10/2006 | Boyer, II ............ B29C 43/006 623/23.63 |
| 7,163,691 B2 | 1/2007 | Knaack et al. |
| 7,252,685 B2 | 8/2007 | Bindseil et al. |
| D553,742 S | 10/2007 | Park |
| D553,743 S | 10/2007 | Park |
| 7,323,011 B2 | 1/2008 | Shepard et al. |
| 7,323,193 B2 | 1/2008 | Morris et al. |
| D566,277 S | 4/2008 | Barry |
| 7,354,452 B2 | 4/2008 | Foley |
| 7,399,739 B2 | 7/2008 | Shimp |
| 7,413,576 B2 | 8/2008 | Sybert et al. |
| D580,551 S | 11/2008 | Cohen et al. |
| 7,491,237 B2 | 2/2009 | Randall et al. |
| 7,537,617 B2 | 5/2009 | Bindsell et al. |
| D595,853 S | 7/2009 | Hanson et al. |
| 7,563,284 B2 | 7/2009 | Coppes et al. |
| 7,645,458 B2 | 1/2010 | Shimp |
| 7,709,018 B2 | 5/2010 | Pastorello et al. |
| D619,255 S | 7/2010 | Richter et al. |
| 7,753,963 B2 | 7/2010 | Boyer, II et al. |
| 7,780,708 B2 | 8/2010 | Morris et al. |
| 7,833,245 B2 | 11/2010 | Kaes et al. |
| 7,837,740 B2 | 11/2010 | Semler et al. |
| 7,857,860 B2 | 12/2010 | Saini et al. |
| 7,931,692 B2 | 4/2011 | Sybert et al. |
| 7,988,733 B2 | 8/2011 | Shimp et al. |
| 8,007,533 B2 | 8/2011 | Zhukauskas et al. |
| 8,157,806 B2 | 4/2012 | Frigg et al. |
| 2002/0038123 A1 | 3/2002 | Visotsky et al. |
| 2003/0009235 A1 | 1/2003 | Manrique et al. |
| 2003/0055511 A1 | 3/2003 | Schryver et al. |
| 2003/0060825 A1 | 3/2003 | Alfaro et al. |
| 2003/0114936 A1 | 6/2003 | Sherwood et al. |
| 2003/0228288 A1 | 12/2003 | Scarborough et al. |
| 2004/0024457 A1 | 2/2004 | Boyce et al. |
| 2004/0115172 A1 | 6/2004 | Bianchi et al. |
| 2005/0015147 A1 | 1/2005 | Schwardt et al. |
| 2005/0065613 A1 | 3/2005 | Gross et al. |
| 2006/0015184 A1 | 1/2006 | Winterbottom et al. |
| 2006/0024656 A1 | 2/2006 | Morris et al. |
| 2006/0280803 A1 | 12/2006 | Kumar et al. |
| 2007/0073293 A1 | 3/2007 | Martz et al. |
| 2007/0088437 A1 | 4/2007 | Betz et al. |
| 2007/0098756 A1 | 5/2007 | Behnam |
| 2007/0154563 A1 | 7/2007 | Behnam et al. |
| 2008/0033572 A1 | 2/2008 | D'Antonio et al. |
| 2008/0058953 A1 | 3/2008 | Scarborough |
| 2008/0234822 A1 | 9/2008 | Govil et al. |
| 2008/0255676 A1 * | 10/2008 | Semler ............... A61F 2/30756 623/23.51 |
| 2009/0018659 A1 | 1/2009 | Malinin |
| 2009/0087471 A1 | 4/2009 | Shimp et al. |
| 2009/0130173 A1 | 5/2009 | Behnam et al. |
| 2009/0149893 A1 | 6/2009 | Semler et al. |
| 2009/0155378 A1 | 6/2009 | Behnam et al. |
| 2009/0227704 A1 | 9/2009 | Troxel et al. |
| 2010/0036413 A1 | 2/2010 | Nakaji |
| 2010/0049326 A1 | 2/2010 | Petersen et al. |
| 2010/0209470 A1 | 8/2010 | Mohan et al. |
| 2010/0274355 A1 | 10/2010 | McGuire et al. |
| 2011/0045044 A1 | 2/2011 | Masinaei et al. |
| 2011/0066241 A1 | 3/2011 | Nauman et al. |
| 2011/0118850 A1 | 5/2011 | Govil et al. |
| 2011/0144766 A1 | 6/2011 | Kale et al. |
| 2011/0182963 A1 | 7/2011 | McKay |
| 2012/0010659 A1 | 1/2012 | Angert et al. |

* cited by examiner

OSTEOGRAFT IMPLANT

This application is a divisional application of U.S. patent application Ser. No. 13/736,490 filed Jan. 8, 2013, entitled "OSTEOGRAFT IMPLANT". This entire disclosure is incorporated herein by reference into the present disclosure.

BACKGROUND

The rapid and effective repair of bone defects caused by injury, disease, wounds, or surgery is a goal of orthopedic surgery. Toward this end, a number of bone implants have been used or proposed for use in the repair of bone defects. The biological, physical, and mechanical properties of the bone implants are among the major factors influencing their suitability and performance in various orthopedic applications.

Bone implants, such as, for example, osteografts, are used to repair bone that has been damaged by disease, trauma, or surgery. Bone implants may be utilized when healing is impaired in the presence of certain drugs or in disease states such as diabetes, when a large amount of bone or disc material is removed during surgery, or when bone fusion is needed to create stability. In some types of spinal fusion, for example, bone implants are used to replace the cushioning disc material between the vertebrae or to repair a degenerative facet joint.

One type of bone implant is an osteograft. Typically, bone graft (e.g., osteograft) materials may include both synthetic and natural bone. Natural bone may be taken from the graft recipient (autograft) or may be taken from another source (allograft), such as a cadaver, or (xenograft), such as bovine. Autografts have advantages such as decreased immunogenicity and greater osteoinductive potential, but there can also be problems with donor site morbidity and limited supply of suitable bone for grafting. On the other hand, allografts are available in greater supply and can be stored for years. However, allografts tend to be less osteoinductive.

Osteoconduction and osteoinduction both contribute to bone formation. A graft material is osteoconductive if it provides a structural framework or microscopic and macroscopic scaffolding for cells and cellular materials that are involved in bone formation (e.g., osteoclasts, osteoblasts, vasculature, mesenchymal cells).

Osteoinductive material, on the other hand, stimulates differentiation of host mesenchymal cells into chondroblasts and osteoblasts. Natural bone osteograft materials can comprise either cortical or cancellous bone. A distinguishing feature of cancellous bone is its high level of porosity relative to that of cortical bone, providing more free surfaces and more of the cellular constituents that are retained on these surfaces. It provides both an osteoinductive and osteoconductive graft material, but generally does not have significant load-bearing capacity. Optimal enhancement of bone formation is generally thought to require a minimum threshold quantity of cancellous bone, however. Cortical (compact) bone has greater strength or load-bearing capacity than cancellous bone, but is less osteoconductive. In humans for example, only approximately twenty percent of large cortical allografts are completely incorporated at five years. Delayed or incomplete incorporation may allow micromotion, leading to host bone resorption around the osteograft. A more optimal bone graft material would combine significant load-bearing capacity with both osteoinductive and osteoconductive properties and much effort has been directed toward developing such a graft material.

Some osteografts comprise mammalian cadaver bone treated to remove all soft tissue, including marrow and blood, and then textured to form a multiplicity of holes of selected size, spacing, and depth. The textured bone section is then immersed and demineralized, for example, in a dilute acid bath. Demineralizing the bone exposes osteoinductive factors, but extensive demineralization of bone also decreases its mechanical strength.

Osteografts have also been formed of organic bone matrix with perforations that extend from one surface, through the matrix, to the other surface to provide continuous channels between opposite surfaces. The organic bone matrix is produced by partial or complete demineralization of natural bone. Although the perforations increase the scaffolding potential of the graft material and may be filled with osteoinductive material as well, perforating organic bone matrix through the entire diameter of the graft decreases its load-bearing capacity.

What is needed is an osteograft that combines the osteoinductive and osteoconductive properties of demineralized bone with the load-bearing capacity provided by cortical osteograft materials. Compositions and methods are needed that facilitate bone remodeling and new bone growth, and integration of the osteograft into host bone.

SUMMARY

In some embodiments, in accordance with the principles of the present disclosure, an osteograft is provided that facilitates bone remodeling and new bone growth, and integration into host bone. The osteograft includes a body comprising cortical bone extending along an axis between a first end and a second end. The body of the osteograft has an outer surface configured to engage host bone of a patient. The body includes at least one recess extending transverse to the axis into the outer surface configured for disposal of an insert. The osteograft includes at least one insert comprising demineralized bone disposed in the at least one recess to initiate the bone fusion process and provide rapid bone bonding to the osteograft. The osteograft of the current application, in some embodiments, is load bearing and provides good mechanical strength.

In some embodiments, in accordance with the principles of the present disclosure, an osteograft is provided that includes a body comprising cortical bone extending between a first end and a second end along an axis. The body of the osteograft includes an outer surface configured to engage host bone of a patient. The body has an upper surface and a lower surface opposite the upper surface and includes an inner surface defining an opening extending through the upper and lower surfaces. The upper and lower surfaces each have a plurality of recesses each having a circular cross-sectional configuration and extending perpendicular to the axis into the outer surface disposed circumferentially about the upper and lower surfaces. The inner surface of the body further includes a plurality of recesses each having a circular cross-sectional configuration and extending parallel to the axis. A plurality of plugs comprising demineralized bone each having a square cross-sectional configuration are disposed in one of the recesses in the osteograft body. The inner and outer surfaces of the osteograft body are surface demineralized before the plugs are disposed into the recesses to promote chemical or cohesive bonding or mechanical press fit between the body and the plugs.

In some embodiments, in accordance with the principles of the present disclosure, a kit is provided that includes an osteograft having a body comprising cortical bone extending between a first end and a second end along an axis. The osteograft includes an outer surface configured to engage host bone of a patient. The body of the osteograft includes upper and lower surfaces and an inner surface defining an opening extending through the upper and lower surfaces. The upper and lower surfaces each have a plurality of recesses extending transverse to the axis into the outer surface. The inner surface has a plurality of recesses extending parallel to the axis into the inner surface. Each of the recesses have a circular cross-sectional configuration. The kit includes a plurality of plugs comprising demineralized bone and having a polygonal cross-sectional configuration configured for disposal in one of the recesses in the body of the osteograft. The kit further includes a plurality of plugs comprising demineralized bone and having a circular cross-sectional configuration configured for disposal in one of the recesses in the body of the osteograft.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1A:
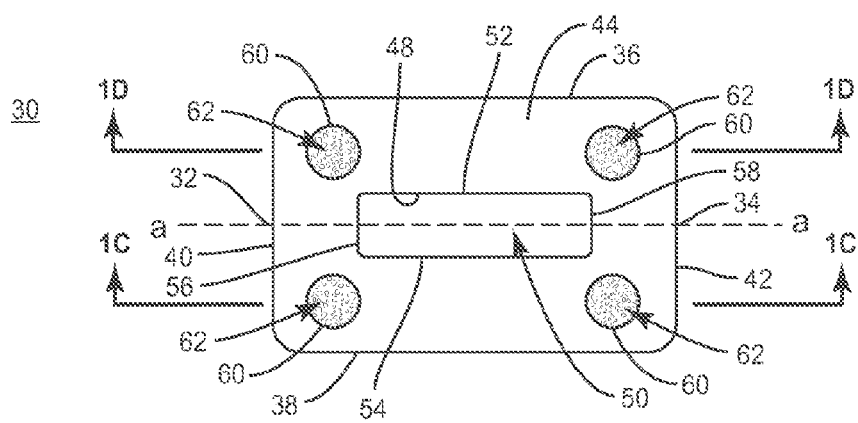
FIG. 1A illustrates a top view of one embodiment of an osteograft in accordance with the principles of the present disclosure.

It is to be understood that the figures are not drawn to scale. Further, the relation between objects in a figure may not be to scale, and may in fact have a reverse relationship

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "an osteograft" includes one, two, three or more osteografts.

The term "biodegradable" includes that all or parts of the implant and/or osteograft will degrade over time by the action of enzymes, by hydrolytic action and/or by other similar mechanisms in the human body. In various embodiments, "biodegradable" includes that the implant and/or osteograft can break down or degrade within the body to non-toxic components after or while a therapeutic agent has been or is being released. By "bioerodible" it is meant that the implant and/or osteograft will erode or degrade over time due, at least in part, to contact with substances found in the surrounding tissue, fluids or by cellular action. By "bioabsorbable" or "bioresorbable" it is meant that the implant and/or osteograft will be broken down and absorbed within the human body, for example, by a cell or tissue. "Biocompatible" means that the osteograft will not cause substantial tissue irritation or necrosis at the target tissue site.

The term "mammal" refers to organisms from the taxonomy class "mammalian," including but not limited to humans, other primates such as chimpanzees, apes, orangutans and monkeys, rats, mice, cats, dogs, cows, horses, etc.

"A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the osteograft is designed for immediate release of biological agents, such as, for example, bone growth materials. In other embodiments the osteograft is designed for sustained release. In other embodiments, the osteograft comprises one or more immediate release surfaces and one or more sustained release surfaces.

The terms "treating" and "treatment" when used in connection with a disease or condition refer to executing a protocol that may include a bone repair procedure, where the osteograft and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or corticocancellous of autogenous, allogenic, xenogenic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, an osteograft seeded with activated MSCs would have the potential to induce bone formation directly, without recruitment and activation of host MSC populations. Because many osteoconductive osteografts also have the ability to bind and deliver bioactive molecules, their osteoinductive potential will be greatly enhanced.

The term "osteograft" or "osteoimplant," as used herein, refers to any bone-derived implant prepared in accordance with the embodiments of this disclosure and therefore is intended to include expressions such as bone membrane, bone graft, etc.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "xenograft" refers to tissue or organs from an individual of one species transplanted into or grafted onto an organism of another species, genus, or family.

The term "demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized." In some embodiments, part or all of the surface of the bone can be demineralized. For example, part or all of the surface of a cortical osteograft can be demineralized to a depth of from about 100 to about 5000 microns, or about 150 microns to about 1000 microns. If desired, the outer surface of the osteograft can be masked with an acid resistant coating or otherwise treated to selectively demineralize unmasked portions of the outer surface of the osteograft so that the surface demineralization is at discrete positions on the osteograft.

The term "demineralized bone matrix," as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the disclosure.

The term "superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The terms "pulverized bone", "powdered bone" or "bone powder" as used herein, refers to bone particles of a wide range of average particle size ranging from relatively fine powders to coarse grains and even larger chips.

The osteograft can comprise bone fibers. Fibers include bone elements whose average length to average thickness ratio or aspect ratio of the fiber is from about 50:1 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are preferably demineralized however some of the original mineral content may be retained when desirable for a particular embodiment.

Non-fibrous, as used herein, refers to elements that have an average width substantially larger than the average thickness of the fibrous bone element or aspect ratio of less than from about 50:1 to about 1000:1. In some embodiments, the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular".

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Osteograft

Osteografts, such as, for example, osteograft 30 are provided that facilitate bone remodeling and new bone growth, and integration of the bone implant (e.g., osteograft) into host bone. In some embodiments, the osteograft provides an improved surface between the dense cortical osteograft and a patient's host bone to facilitate incorporation of the osteograft construct and fusion to host bone. In some embodiments, the osteograft comprises includes recesses extending into an outer surface of the osteograft having inserts comprising demineralized bone inserted into the recesses to initiate the bone fusion process at the osteograft surface and provide rapid bone bonding to the cortical osteograft. The osteograft of the current application, in some embodiments, is load bearing and provides good mechanical strength.

Osteograft 30 includes a body having a substantially rectangular configuration comprising cortical bone extending along an axis a between a first end 32 and a second end 34. In addition to bone, such as, for example, cortical bone, osteograft 30 may comprise natural and/or synthetic materials. For example, osteograft 30 may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, or combinations thereof.

In some embodiments, osteograft 30 may comprise a resorbable ceramic (e.g., hydroxyapatite, tricalcium phosphate, bioglasses, calcium sulfate, etc.) tyrosine-derived polycarbonate poly(DTE-co-DT carbonate), in which the pendant group via the tyrosine—an amino acid—is either an ethyl ester (DTE) or free carboxylate (DT) or combinations thereof.

In some embodiments, osteograft 30 may comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

Osteograft 30 may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, osteograft 30 has a density of between about 1.6 g/cm$^3$, and about 0.05 g/cm$^3$. In some embodiments, osteograft 30 has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of osteograft 30 may be tailored to the site at which it is to be situated. For example, it may be in the shape of a morsel, a plug, a pin, a peg, a cylinder, a block, a wedge, ring, a sheet, etc. In some embodiments, osteograft 30 is H-shaped for placement between the spinous process.

In some embodiments, osteograft 30 may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

The body of osteograft 30 includes parallel side walls 36, 38 extending between ends 32, 34 on opposite sides of osteograft 30. The body of osteograft 30 includes a first end wall 40 at end 32 extending between side walls 36, 38 and a second end wall 42 at end 34 extending between side walls 36, 38. End walls 40, 42 are parallel to one another. The body of osteograft 30 further includes a top surface 44 and a bottom surface 46 opposite surface 44 each extending transverse to axis a. Surfaces 44, 46 are parallel to one another. It is envisioned that osteograft 30 may have alternate cross section configurations, such as, for example, oval, oblong, triangular, square, hexagonal, polygonal, irregular, uniform, non-uniform and/or tapered. It is further envisioned that side walls 36, 38 and/or end walls 40, 42 and/or surfaces 44, 46 may be disposed at alternate orientations, relative to one another, such as, for example, transverse and/or other angular orientations such as acute or obtuse, according to the requirements of a particular application. It is contemplated that the body of the graft is not demineralized in order to provide structural support.

In some embodiments, corners of osteograft 30 between side wall 36 and end wall 40, between side wall 36 and end wall 42, between side wall 38 and end wall 40 and between side wall 38 and end wall 42 are rounded to facilitate insertion of osteograft 30 into a patient, such as, for example, between adjacent vertebrae, without damaging tissue or other portions of the patient's anatomy. It is envisioned that corners of osteograft 30 between side wall 36 and end wall 40, between side wall 36 and end wall 42, between side wall 38 and end wall 40 and between side wall 38 and end wall 42 may be non-rounded, depending upon the requirements of a particular application.

In some embodiments, osteograft 30 includes an inner surface 48 defining a passage 50 extending through top and bottom surfaces 44, 46. Passage 50 has a substantially rectangular cross sectional configuration defined by parallel side walls 52, 54 extending between parallel end walls 56, 58. It is envisioned that passage 50 may have alternate cross section configurations, such as, for example, circular, oval, oblong, triangular, square, hexagonal, polygonal, irregular, uniform, non-uniform and/or tapered. It is further envisioned that side walls 52, 54 and/or end walls 56, 58 may be disposed at alternate orientations, relative to one another, such as, for example, transverse and/or other angular orientations such as acute or obtuse, according to the requirements of a particular application. It is further envisioned that passage 50 may have alternate cross section configurations, such as, for example, oval, oblong, triangular, square, hexagonal, polygonal, irregular, uniform, non-uniform and/or tapered.

The body of osteograft 30 has an outer surface configured to engage host bone of a patient. The body includes at least one recess 60 extending transverse to axis a into the outer surface of osteograft 30 configured for disposal of an insert, such as, for example a plug 62 comprising demineralized bone to initiate the bone fusion process and bone bonding. That is, plugs 62 provide a sufficient amount of osteoinductive and/or osteoconductive material, such as, for example, demineralized bone matrix, to initiate the fusion process at an interface between osteograft 30 and plugs 62 to promote rapid bone bonding to osteograft 30.

Figure 1B:
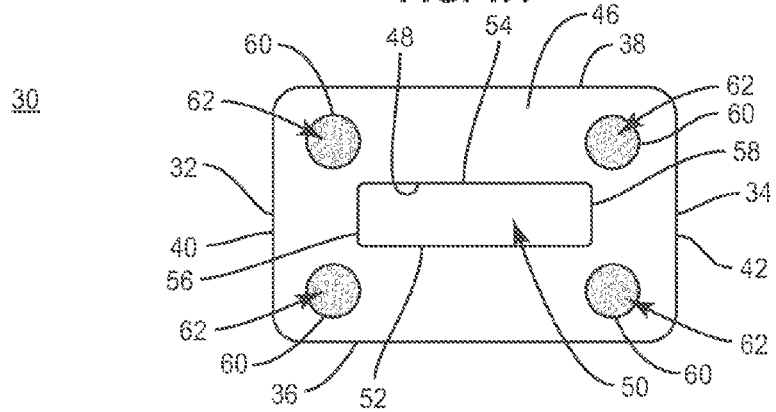
FIG. 1B illustrates a bottom view of the osteograft shown in FIG. 1A.
Figure 1C:
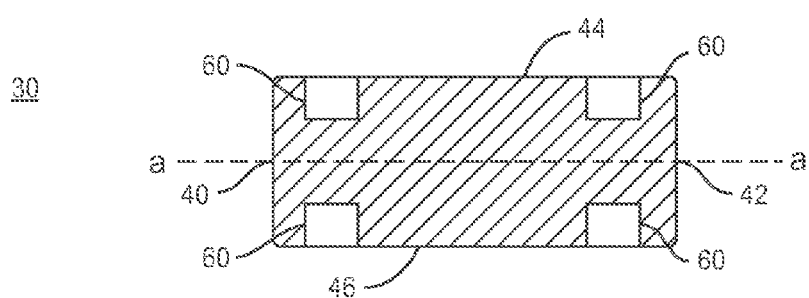
FIG. 1C illustrates a side cross sectional view of the osteograft shown in FIG. 1A.
Figure 1D:
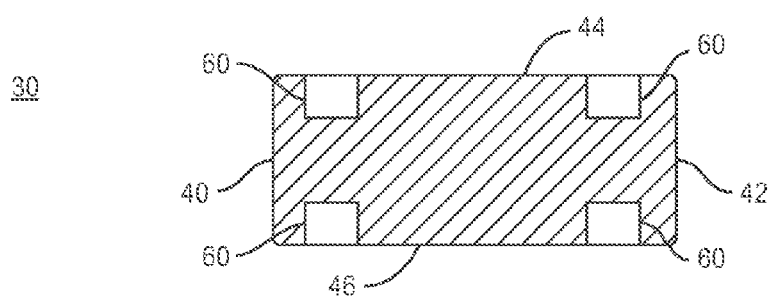
FIG. 1D illustrates a side cross sectional view of the osteograft shown in FIG. 1A.

Recesses 60 may be drilled or machined into selected portions of osteograft 30. Recesses 60 have a circular cross sectional configuration and extend transverse to axis a. Osteograft 30 includes a plurality of spaced apart recesses 60 in top surface 44 (FIG. 1A) and a plurality of spaced apart recesses 60 in bottom surface 46 (FIG. 1B). Recesses 60 are uniformly distributed on top surface 44 and bottom surface 46. In particular, osteograft 30 includes a recess 60 in corners of top and bottom surfaces 44, 46 between side wall 36 and end wall 40, between side wall 36 and end wall 42, between side wall 38 and end wall 40 and between side wall 38 and end wall 42 such that recesses 60 in top surface 44 are coaxial with recesses 60 in bottom surface 46 (FIGS. 1C and 1D). It is envisioned that top surface 44 may include one or a plurality of recesses 60 that are each coaxial with an equal number of recesses 60 in bottom surface 46. This configuration allows for a plug 62 comprising a material, such as, for example, demineralized bone inserted into recesses 60 to simultaneously distribute osteoconductive and/or osteoinductive material in the same amount and manner from top surface 44 as bottom surface 46. It is further envisioned that recesses 60 may be disposed in top surface 44 and/or bottom surface 46 at alternate orientations, relative to axis a, such as, for example, perpendicular and/or other angular orientations such as acute or obtuse, according to the requirements of a particular application. It is contemplated that at least a portion of the body of osteograft 30 may be surface demineralized to promote chemical or cohesive bonding between the body and plug(s) 62.

In some embodiments, osteograft 30 includes recesses 60 in side walls 52, 54 extending transverse to axis a and plugs 62 disposed in such recesses 60. End walls 52, 54 may each include one or a plurality of recesses 60 therein. Side wall 52 includes a plurality of recesses 60 that are each coaxial with recesses 60 in side wall 54. This configuration allows for a plug 62 comprising a material, such as, for example, demineralized bone inserted into recesses 60 in side walls 52, 54 to simultaneously distribute osteoconductive and/or osteoinductive material in the same amount and manner from side wall 52 as side wall 54 such that the osteoconductive and/or osteoinductive material(s) may be substantially uniformly distributed in passage 50. It is envisioned that side wall 52 may include one or a plurality of recesses 60 that are not coaxial with any recesses in side wall 54. This configuration allows for a plug 62 comprising a material, such as, for example, demineralized bone inserted into recesses 60 in side walls 52, 54 to simultaneously distribute osteoconductive and/or osteoinductive material in different amounts and directions from side wall 52 than side wall 54 such that the osteoconductive and/or osteoinductive material(s) may be substantially uniformly distributed in passage 50. It is further envisioned that side wall 52 may include one or a plurality of recesses 60 that are coaxial with recesses 60 in side wall 54 and one or a plurality of recesses 60 that are not coaxial with recesses 60 in side wall 54. It is contemplated that recesses 60 may be disposed in side walls 52, 54 at alternate orientations, relative to axis a, such as, for example, perpendicular and/or other angular orientations such as acute or obtuse, according to the requirements of a particular application.

Figure 2A:
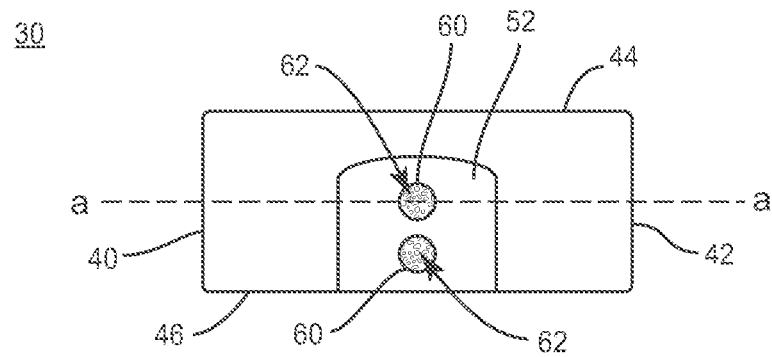
FIG. 2A illustrates a side cross sectional view of one embodiment of an inner surface of the osteograft shown in FIG. 1A.
Figure 2B:
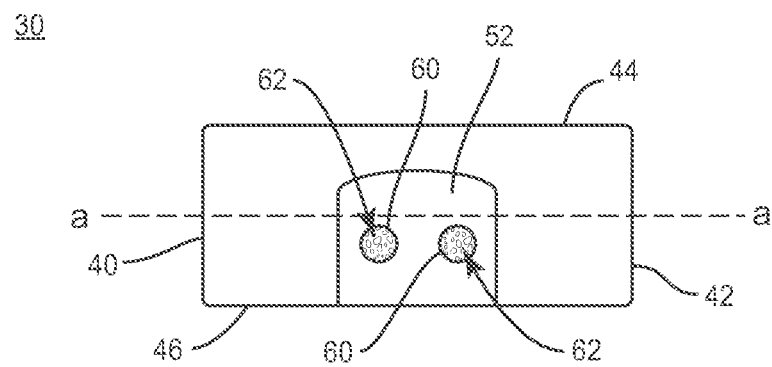
FIG. 2B illustrates a side cross sectional view of one embodiment of an inner surface of the osteograft shown in FIG. 1A.
Figure 2C:
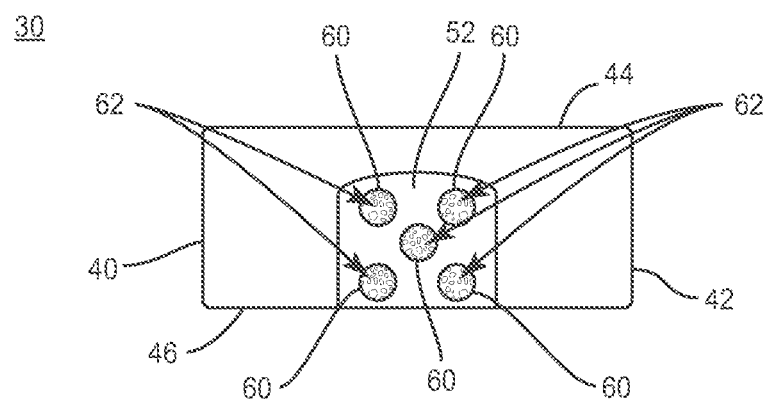
FIG. 2C illustrates a side cross sectional view of one embodiment of an inner surface of the osteograft shown in FIG. 1A.

In some embodiments, side walls 52, 54 each include a plurality of recesses 60 that are parallel to one another extending along an axis that is perpendicular to axis a (FIG. 2A). In one embodiment, side walls 52, 54 each include a plurality of recesses 60 that are parallel to one another extending along an axis that is parallel to axis a (FIG. 2B). In one embodiment, side walls 52, 54 each include a plurality of recesses 60 arranged in geometric pattern (FIG. 2C).

In some embodiments, osteograft 30 includes recesses 60 in end walls 56, 58 extending parallel with axis a and plugs 62 disposed in such recesses 60. End walls 56, 58 may each include one or a plurality of recesses 60 therein. End wall 56 includes a plurality of recesses 60 that are each coaxial with recesses 60 in end wall 58. This configuration allows for a plug 62 comprising a material, such as, for example, demineralized bone inserted into recesses 60 in end walls 56, 58 to simultaneously distribute osteoconductive and/or osteoinductive material in the same amount and manner from end wall 56 as end wall 58 such that the osteoconductive and/or osteoinductive material(s) may be substantially uniformly distributed in passage 50. It is envisioned that end wall 56 may include one or a plurality of recesses 60 that are not coaxial with any recesses in end wall 58. This configuration allows for a plug 62 comprising a material, such as, for example, demineralized bone inserted into recesses 60 in end walls 56, 58 to simultaneously distribute osteoconductive and/or osteoinductive material in different amounts and directions from end wall 56 than end wall 58 such that the osteoconductive and/or osteoinductive material(s) may be substantially uniformly distributed in passage 50. It is further envisioned that end wall 56 may include one or a plurality of recesses 60 that are coaxial with recesses 60 in end wall 58 and one or a plurality of recesses 60 that are not coaxial with recesses 60 in end wall 58. It is contemplated that recesses 60 may be disposed in end walls 56, 58 at alternate orientations, relative to axis a, such as, for example, transverse, perpendicular and/or other angular orientations such as acute or obtuse, according to the requirements of a particular application.

Figure 3A:
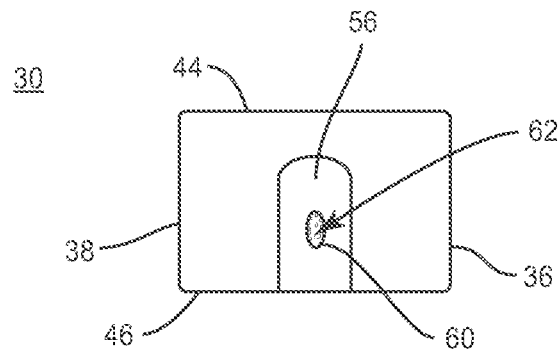
FIG. 3A illustrates a side cross sectional view of one embodiment of an inner surface of the osteograft shown in FIG. 1A.
Figure 3B:
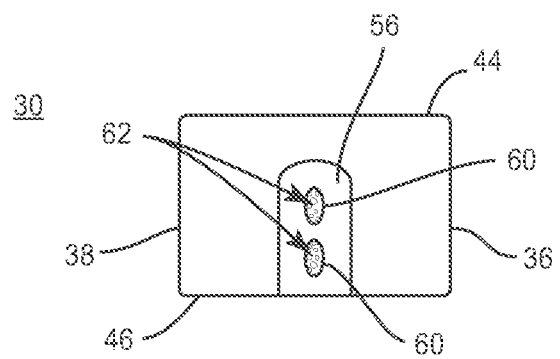
FIG. 3B illustrates a side cross sectional view of one embodiment of an inner surface of the osteograft shown in FIG. 1A.
Figure 3C:
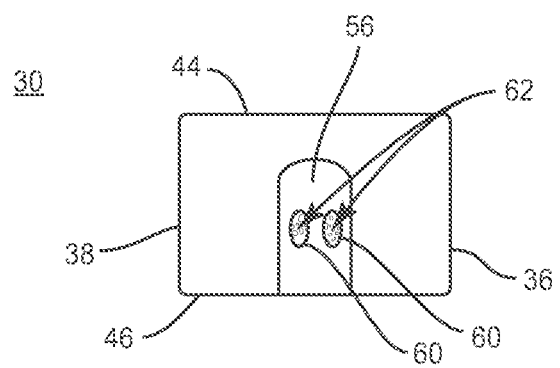
FIG. 3C illustrates a side cross sectional view of one embodiment of an inner surface of the osteograft shown in FIG. 1A.

In some embodiments, end walls 56, 58 each include a single recess 60 (FIG. 3A). The recesses 60 in end walls 56, 58 are coaxial with one another. It is envisioned that the single recess 60 in end walls 56, 58 may be disposed equidistant from top and bottom surfaces 44, 46, may be disposed closer to top surface 44 than bottom surface 46, or may be disposed closer to bottom surface 46 than top surface, depending upon the location in which osteoconductive and/or osteoinductive material. For example, if a particular application requires that more osteoconductive and/or osteoinductive material be delivered adjacent top surface 44 than bottom surface 46, recesses 60 in end walls 56, 58 may be disposed closer to top surface 44 than bottom surface 46. It is further envisioned that the recesses 60 in end walls 56, 58 may be offset from one another. In one embodiment, end walls 56, 58 each include a plurality of recesses 60 that are parallel to one another extending along an axis extending perpendicular to top surface 44 (FIG. 3B). In one embodiment, end walls 56, 58 each include a plurality of recesses 60 that are parallel to one another extending along an axis extending parallel to top surface 44 (FIG. 3C).

In some embodiments, plugs 62 comprise demineralized cancellous bone. It is envisioned that plugs 62 may also comprise demineralized cortical bone, a combination of demineralized cancellous bone and demineralized cortical bone, a combination of demineralized cancellous bone and non-demineralized cortical bone, or a combination of non-demineralized cancellous bone and demineralized cortical bone.

In some embodiments, plugs 62 comprise demineralized bone matrix. It is envisioned that plugs 62 may comprise demineralized bone matrix fibers and demineralized bone matrix powder. It is further envisioned that plugs 62 may comprise demineralized bone matrix fibers and demineralized bone matrix powder in a ratio of 25:75 to about 75:25 fibers to chips.

In some embodiments, plugs 62 are surface demineralized to provide a more conducive surface for the demineralized bone to attach to via both friction and cohesive binding of collagen/protein compositions to osteograft 30. The healing process also exposes some of the inherent bone growth factors to further facilitate remodeling and new bone formation. The surface demineralization of plugs 62 provides an easier route of entry for bone remodeling to occur in the osteograft 30 further facilitating faster fusion.

Demineralized bone matrix (DBM) is demineralized bone with osteoinductive activity. DBM is prepared by acid extraction of osteograft bone, resulting in loss of most of the mineralized component but retention of collagen and non-collagenous proteins, including growth factors. DBM does not contain osteoprogenitor cells, but the efficacy of a demineralized bone matrix may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (e.g. glycerol or a polymer). DBM is mostly an osteoinductive product, but lacks enough induction to be used on its own in challenging healing environments such as posterolateral spine fusion.

In some embodiments, the depth of surface demineralization in plugs 62 may be between about 50 to about 5000 microns, or about 100 microns to about 1000 microns or about 2000 microns. If desired, the outer surfaces of plugs 62 can be masked with an acid resistant coating or otherwise treated to selectively demineralize unmasked portions of the outer surface of plugs 62 so that the surface demineralization is at discrete positions on plugs 62.

In some embodiments, plugs 60 are coated with demineralized bone, such as, for example demineralized bone matrix. The demineralized bone is applied to the surface of plug 62 and allowed to bind via air drying, or alternatively freeze dried, heat drying, or a mild chemical crosslinking agent or adhesive can be used. The form of the DBM can be chips, shards, powders, fibers or a combination thereof, which are osteoinductive. In some embodiments, each plug 62 can have both surface demineralization and DBM chips, shards, powders, or a combination thereof disposed on its surface.

In one embodiment, DBM powder can range in average particle size from about 0.0001 to about 1.2 cm and from about 0.002 to about 1 cm. The bone powder can be obtained from cortical, cancellous and/or corticocancellous allogenic or xenogenic bone tissue. In general, allogenic bone tissue is preferred as the source of the bone powder.

In some embodiments, the coating thickness of DBM powder and/or fibers on plugs 62 may be thin, for example, from about 5, 10, 15, 20, 25, 30, 35, 40, 45 or 50 microns to thicker coatings 60, 65, 70, 75, 80, 85, 90, 95, 100 microns. In some embodiments, the range of the coating ranges from about 5 microns to about 250 microns or 5 microns to about 200 microns.

According to some embodiments of the disclosure, the demineralized bone matrix may comprise demineralized bone matrix fibers and/or demineralized bone matrix chips. In some embodiments, the demineralized bone matrix may comprise demineralized bone matrix fibers and demineralized bone matrix chips in a 30:60 ratio. In different embodiments of the disclosure, bone powder content can range from about 5% to about 90% w/w, polymer content can range from about 5% to about 90% w/w, and demineralized bone particles content comprises the reminder of the composition. Preferably, the demineralized bone particles comprise from about 20% to about 40% w/w while the polymer and the bone powder comprise each from about 20% to about 60% w/w of the composition. The bone graft materials of the present disclosure include those structures that have been modified in such a way that the original chemical forces naturally present have been altered to attract and bind molecules, including, without limitation, growth factors and/or cells, including cultured cells.

The demineralized bone that makes up plugs 62 may be further modified such that the original chemical forces naturally present have been altered to attract and bind growth factors, other proteins and cells affecting osteogenesis, osteoconduction and osteoinduction. For example, a demineralized bone material may be modified to provide an ionic gradient to produce a modified demineralized bone material, such that implanting plugs 62 including the modified demineralized bone material results in enhanced ingrowth of host bone.

In one embodiment an ionic force change agent may be applied to modify the demineralized bone material. The demineralized allograft bone material may comprise, e.g., a demineralized bone matrix (DBM) comprising fibers, particles and any combination of thereof. According to another embodiment, a bone graft structure may be used which comprises a composite bone, which includes a bone powder, a polymer and a demineralized bone.

The ionic force change agent may be applied to the entire demineralized bone material or to selected portions/surfaces thereof. The ionic force change agent may be a binding agent, which modifies the demineralized bone material to bind molecules, such as, for example, DBM, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7 (OP-1), rhBMP-7, GDF-5, LIM mineralization protein, platelet derived growth factor (PDGF), transforming growth factor-β (TGF-β), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

An adhesive may be applied to the DBM powders and/or fibers to adhere the DBM powders and/or fibers to the outer surface of plugs 62 and/or to form plugs 62. The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (e.g., hydroxypropylcellulose). In some embodiments, the synthetic polymers having a carboxyl group, may comprise poly(acrylic acid), poly(methacrylic acid), poly (vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyl-disulfide, maleimide, aldehyde, iodoacetamide or a combination thereof. In some embodiments, the adhesive material can comprise at least one of fibrin, a cyanoacrylate (e.g., N-butyl-2-cyanoacrylate, 2-octyl-cyanoacrylate, etc.), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers as mentioned in U.S. Pat. No. 4,708,821. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site, cannula and/or expandable member. In some embodiments, to have the device adhere to the target tissue site, pressure is applied in a direction substantially perpendicular to a surgical incision.

Multi-component adhesives harden by mixing two or more components, which chemically react. This reaction causes polymers to cross-link into acrylics, urethanes, and/or epoxies. There are several commercial combinations of multi-component adhesives in use in industry. Some of these combinations are: polyester resin-polyurethane resin; polyols-polyurethane resin, acrylic polymers-polyurethane resins or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied (e.g., body heat), the components react and cross-link. This type of adhesive includes epoxies, urethanes, and/or polyimides. The adhesive can be a moisture curing adhesive that cures when it reacts with moisture present (e.g., bodily fluid) on the substrate surface or in the air. This type of adhesive includes cyanoacrylates or urethanes. The adhesive can have natural components, such as for example, vegetable matter, starch (dextrin), natural resins or from animals e.g. casein or animal glue. The adhesive can have synthetic components based on elastomers, thermoplastics, emulsions, and/or thermosets including epoxy, polyurethane, cyanoacrylate, or acrylic polymers.

In some embodiments, the body of osteograft 30 comprises an allograft and the body of osteograft 30 and plugs 62 each comprise bone material obtained from the same donor. In some embodiments, the body of osteograft 30 comprises an allograft and plugs 62 each comprise bone material obtained from the patient. In some embodiments, the body of osteograft 30 comprises an autograft and the body of osteograft 30 and plugs 62 each comprise bone material obtained from the patient. These configurations allow new bone to form quickly because host bone does not have to go through the process of osteoclastic resorption first, resulting in faster stabilization of osteograft 30 and fusion.

Figure 4A:
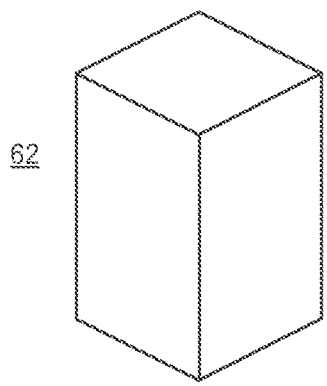
FIG. 4A illustrates a perspective view of one embodiment of an insert of the osteograft shown in FIG. 1A in accordance with the principles of the present disclosure.
Figure 4B:
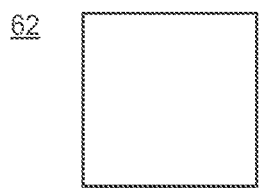
FIG. 4B illustrates a top view of the insert shown in FIG. 10A.
Figure 5:
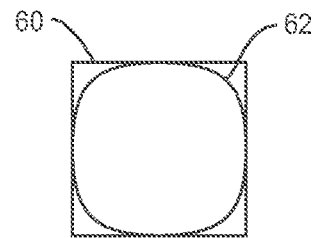
FIG. 5 illustrates the insert shown in FIG. 10A positioned within a recess of the osteograft shown in FIG. 1A.

In some embodiments, recesses 60 have a circular cross sectional configuration and plugs 62 have a polygonal cross sectional configuration, such as, for example, square (FIGS. 4A and 4B). Plugs 62 comprise demineralized cancellous bone and the body of osteograft 30 comprises cortical bone, as discussed above. The width of plugs 62 is substantially equivalent to the diameter of recesses 60 such that plugs 62 are press fit into recesses 60 (FIG. 5). It is envisioned that the width of plugs 62 may also be greater than to the diameter of recesses 60 to improve fixation of plugs 62 within recesses 60. It is further envisioned that plugs 62 may also have a width that is less than the diameter of recesses 60 to facilitate insertion of plugs 62 into recesses 60. It is contemplated that plugs 62 may have a height that is substantially equivalent to a depth of recesses 60 to ensure that plugs 62 are completely disposed within recesses 60. It is further contemplated that plugs 62 may have a height that is greater than a depth of recesses 60 to increase the amount of osteoinductive and/or osteoinductive material disposed in recesses 60.

In some embodiments, plugs 62 are sufficiently demineralized allowing plugs 62 to deform such that plugs 62 can be inserted into recesses 60 having a maximum width that is less than a maximum width of plugs 62. This configuration allows pressure to be applied to plugs 62, such as, for example, by squeezing plugs 62 as plugs 62 are inserted into recesses 60. Once pressure is released, plugs 62 expand within recesses 60 to maintain plugs 62 in recesses 60. In some embodiments, plugs 62 comprise from about 1% to about 30% or from about 5% to about 25% by weight of demineralized bone material.

Figure 6A:
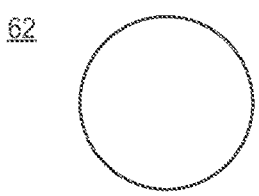
FIG. 6A illustrates a perspective view of one embodiment of an insert of the osteograft shown in FIG. 1A in accordance with the principles of the present disclosure.
Figure 6B:
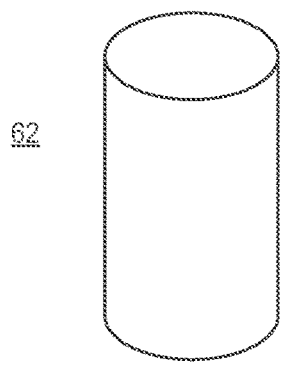
FIG. 6B illustrates a top view of the insert shown in FIG. 11A.

In some embodiments, recesses 60 have a circular cross sectional configuration and plugs 62 have a circular cross sectional configuration (FIGS. 6A and 6B). Plugs 62 comprise demineralized cancellous bone and the body of osteograft 30 comprises cortical bone, as discussed above. The diameter of plugs 62 is greater than the diameter of recesses 60 such that plugs 62 are press fit into recesses 60. It is envisioned that the width of plugs 62 may also be substantially equivalent to the diameter of recesses 60 to facilitate insertion of plugs 62 into recesses 60.

Figure 7A:
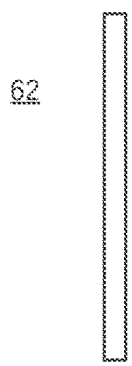
FIG. 7A illustrates a side view of one embodiment of an insert of the osteograft shown in FIG. 1A in accordance with the principles of the present disclosure.
Figure 7B:
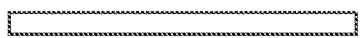
FIG. 7B illustrates a side view of the insert shown in FIG. 12A.

In some embodiments, plugs 62 comprise strips of demineralized bone (FIGS. 7A and 7B). Plugs 62 comprise demineralized cancellous bone and the body of osteograft 30 comprises cortical bone, as discussed above. Recesses 60 have a volume sufficient for disposal of a plurality of plugs 62, when plugs 62 are in the form of strips. It is envisioned that plugs 62, when in the form of strips, are sufficiently flexible such that a plurality of plugs 62 can packed into each recess 60. It is further envisioned that plugs, 62, when in the form of strips, have a length that is greater than a width and/or depth of recesses 60, but can be squeezed to decrease the length thereof such that the length of plugs 62 is less than the width and/or the depth of recesses 60. Plugs 62 would then expand following insertion into recesses 60 to maintain plugs 62 within recesses 60.

Figure 8A:
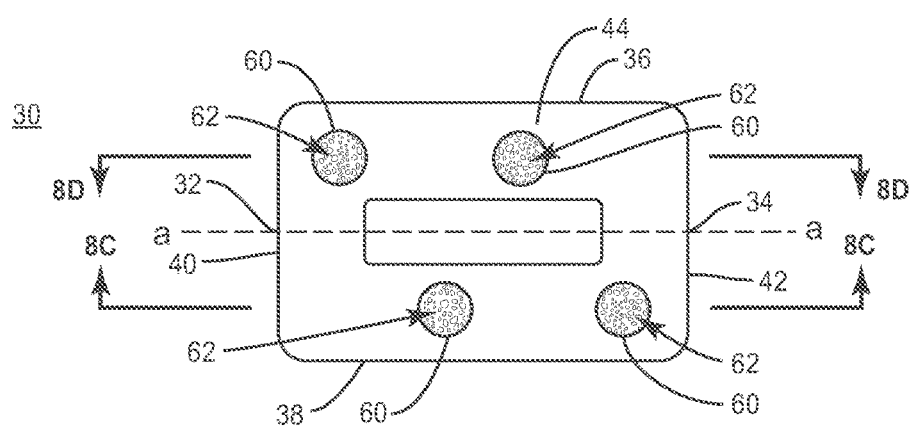
FIG. 8A illustrates a top view of one embodiment of an osteograft in accordance with the principles of the present disclosure.
Figure 8B:
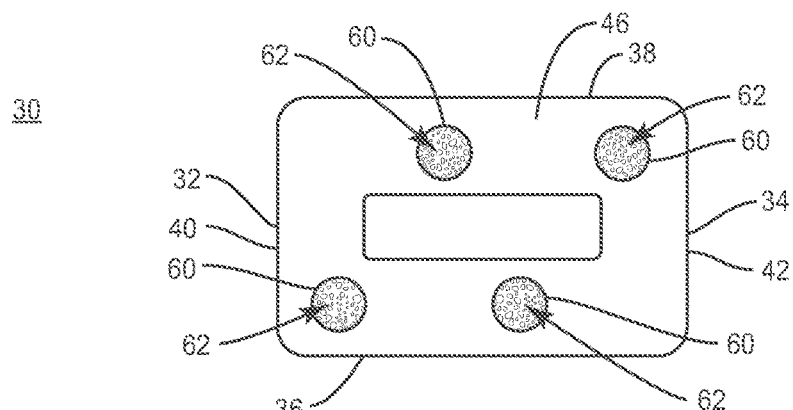
FIG. 8B illustrates a bottom view of the osteograft shown in FIG. 8A.
Figure 8C:
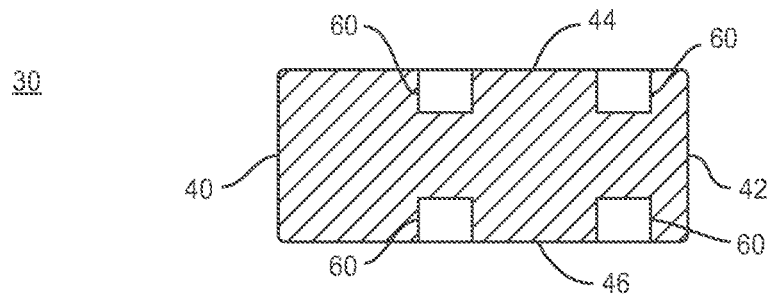
FIG. 8C illustrates a side cross sectional view of the osteograft shown in FIG. 8A.
Figure 8D:
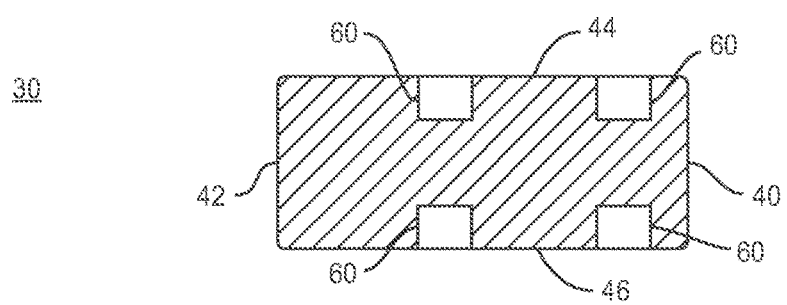
FIG. 8D illustrates a side cross sectional view of the osteograft shown in FIG. 8A.

In some embodiments, osteograft 30 includes a plurality of spaced apart recesses 60 in top surface 44 (FIG. 8A) and a plurality of spaced apart recesses 60 in bottom surface 46 (FIG. 8B). Osteograft 30 includes at least one recess 60 in corners of top and bottom surfaces 44, 46 between side wall 36 and end wall 40 and between side wall 38 and end wall 42. Osteograft 30 also includes at least one recess 60 that is parallel with the recess(es) 60 in corners of top and bottom surfaces 44, 46 between side wall 36 and end wall 40 along axis a and at least one recess 60 that is parallel with the recess(es) 60 in corners of top and bottom surfaces 44, 46 between side wall 38 and end wall 42 along axis a such that recesses 60 in top surface 44 are coaxial with recesses 60 in bottom surface 46 (FIGS. 8C and 8D). This configuration allows for a plug 62 comprising a material, such as, for example, demineralized bone inserted into recesses 60 to simultaneously distribute osteoconductive and/or osteoinductive material in the same amount and manner from top surface 44 as bottom surface 46.

Figure 9A:
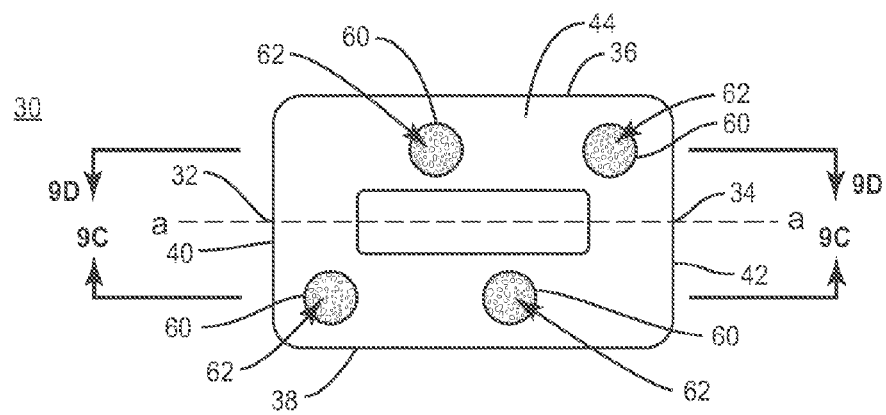
FIG. 9A illustrates a top view of one embodiment of an osteograft in accordance with the principles of the present disclosure.
Figure 9B:
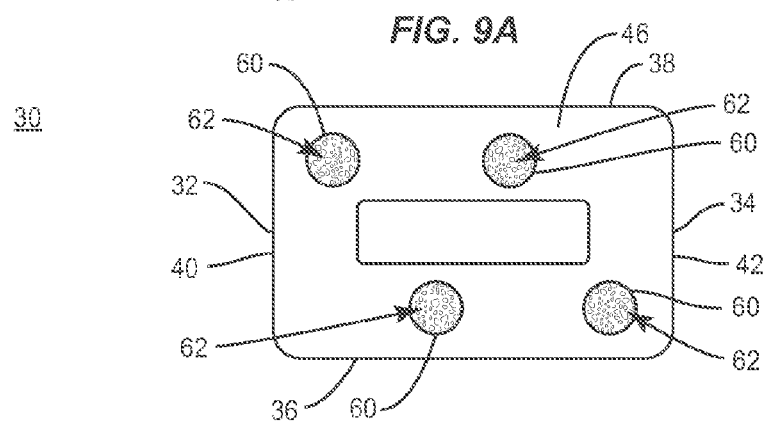
FIG. 9B illustrates a bottom view of the osteograft shown in FIG. 9A.
Figure 9C:
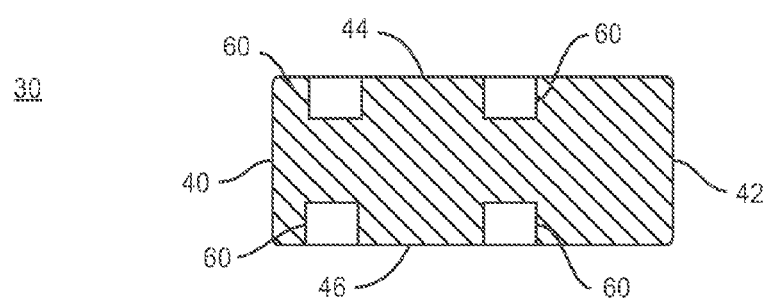
FIG. 9C illustrates a side cross sectional view of the osteograft shown in FIG. 9A.
Figure 9D:
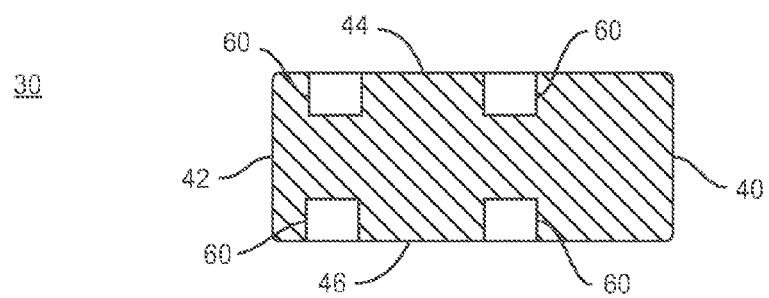
FIG. 9D illustrates a side cross sectional view of the osteograft shown in FIG. 9A.

In some embodiments, osteograft 30 includes a plurality of spaced apart recesses 60 in top surface 44 (FIG. 9A) and a plurality of spaced apart recesses 60 in bottom surface 46 (FIG. 9B). Osteograft 30 includes at least one recess 60 in corners of top and bottom surfaces 44, 46 between side wall 36 and end wall 42 and between side wall 38 and end wall 40. Osteograft 30 also includes at least one recess 60 that is parallel with the recess(es) 60 in corners of top and bottom surfaces 44, 46 between side wall 36 and end wall 42 along axis a and at least one recess 60 that is parallel with the recess(es) 60 in corners of top and bottom surfaces 44, 46 between side wall 38 and end wall 40 along axis a such that recesses 60 in top surface 44 are coaxial with recesses 60 in bottom surface 46 (FIGS. 9C and 9D). This configuration allows for a plug 62 comprising a material, such as, for example, demineralized bone inserted into recesses 60 to simultaneously distribute osteoconductive and/or osteoinductive material in the same amount and manner from top surface 44 as bottom surface 46.

Figure 10A:
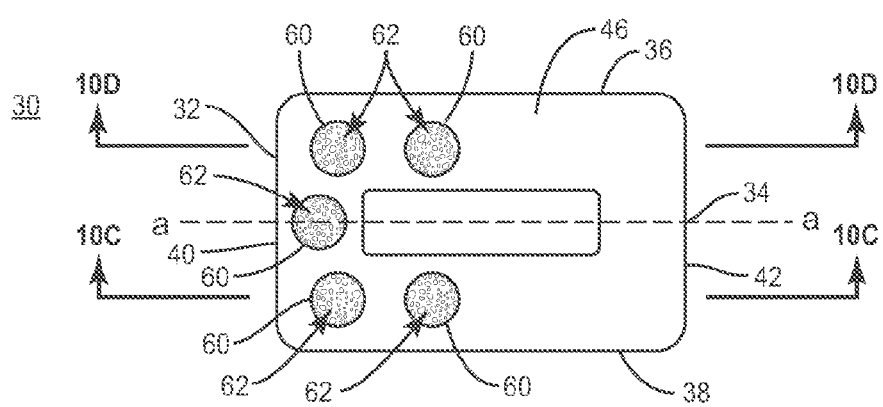
FIG. 10A illustrates a top view of one embodiment of an osteograft in accordance with the principles of the present disclosure.
Figure 10B:
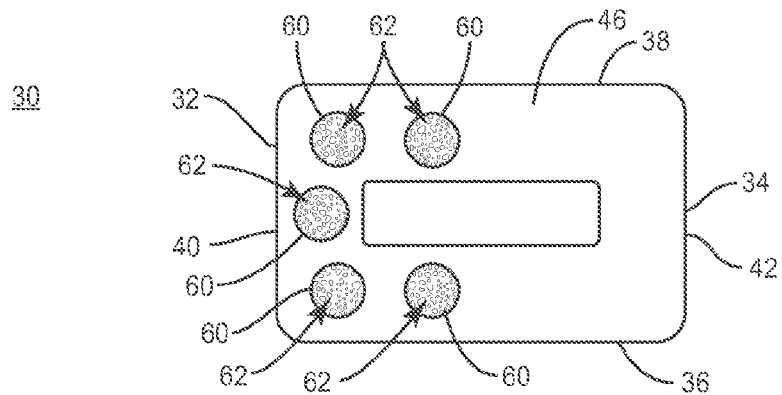
FIG. 10B illustrates a bottom view of the osteograft shown in FIG. 10A.
Figure 10C:
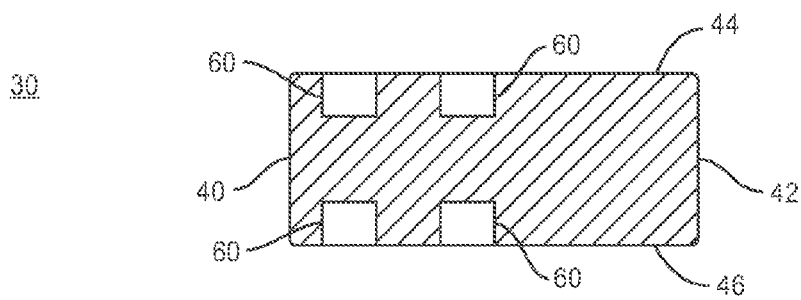
FIG. 10C illustrates a side cross sectional view of the osteograft shown in FIG. 10A.
Figure 10D:
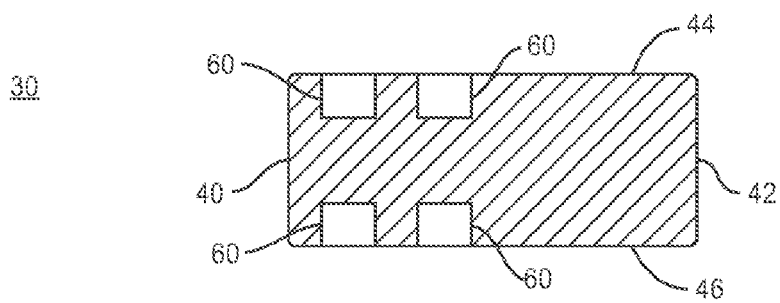
FIG. 10D illustrates a side cross sectional view of the osteograft shown in FIG. 10A.

In some embodiments, osteograft 30 includes a plurality of spaced apart recesses 60 in top surface 44 (FIG. 10A) and a plurality of spaced apart recesses 60 in bottom surface 46 (FIG. 10B). Osteograft 30 includes at least one recess 60 in top and bottom surfaces 44, 46 positioned closer to end 32 than end 34. Osteograft 30 does not include any recesses 60 in top and bottom surfaces 44, 46 adjacent end 34. It is envisioned that recesses 60 in top and bottom surfaces 44, 46 may alternatively be positioned closer to end 34 than end 32. It is further envisioned that the that recesses 60 in top surface 44 may be coaxial with recesses 60 in bottom surface 46 (FIGS. 10C and 10D). This configuration allows for a plug 62 comprising a material, such as, for example, demineralized bone inserted into recesses 60 to distribute osteoconductive and/or osteoinductive material from top surface 44 and bottom surface 46 to a particular location, such as, for example, a lateral side of an intervertebral space, without directly distributing osteoconductive and/or osteoinductive material to other adjacent locations, such as, for example, an opposite lateral side of the intervertebral space. It is envisioned that this configuration also avoids osteograft subsidence.

Figure 11A:
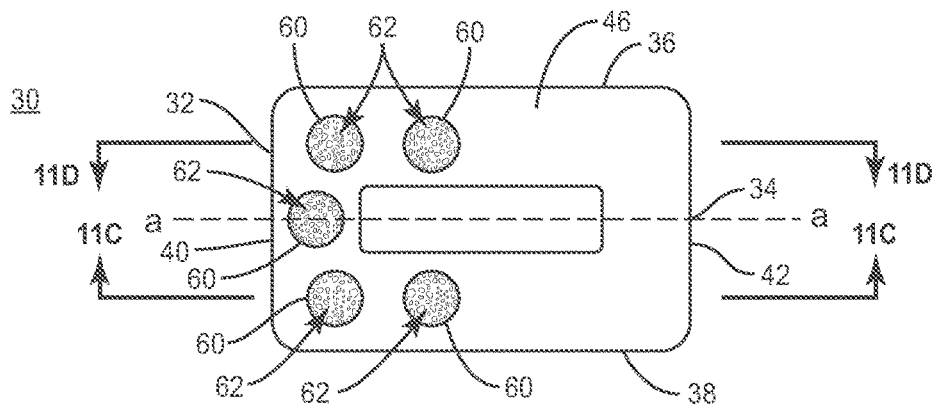
FIG. 11A illustrates a top view of one embodiment of an osteograft in accordance with the principles of the present disclosure.
Figure 11B:
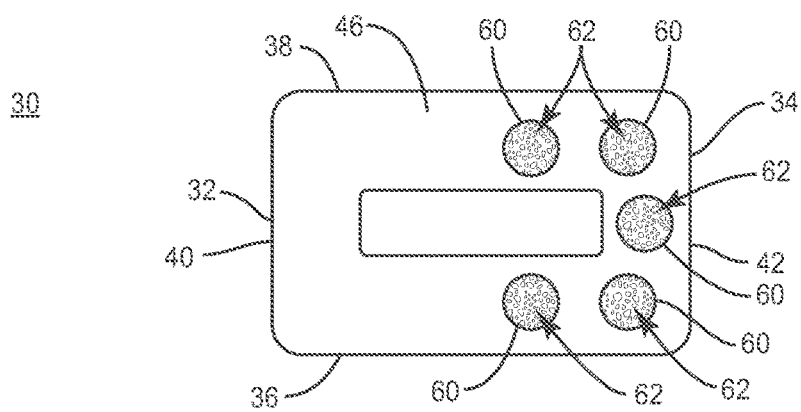
FIG. 11B illustrates a bottom view of the osteograft shown in FIG. 11A.
Figure 11C:
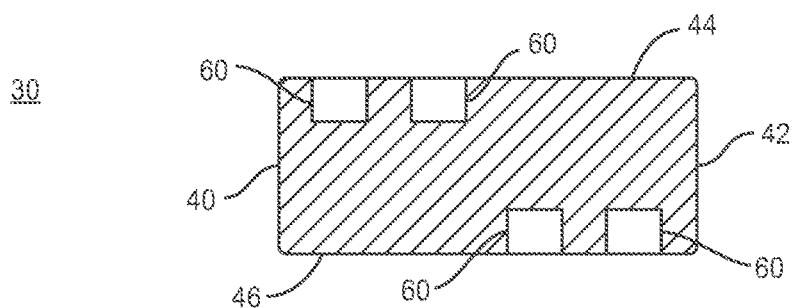
FIG. 11C illustrates a side cross sectional view of the osteograft shown in FIG. 11A.
Figure 11D:
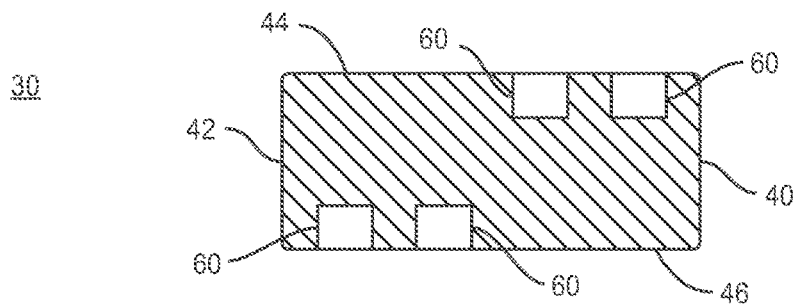
FIG. 11D illustrates a side cross sectional view of the osteograft shown in FIG. 11A.

In some embodiments, osteograft 30 includes a plurality of spaced apart recesses 60 in top surface 44 (FIG. 11A) and a plurality of spaced apart recesses 60 in bottom surface 46 (FIG. 11B). Osteograft 30 includes at least one recess 60 in top surface 44 positioned closer to end 32 than end 34 and at least one recess 60 in bottom surface 46 positioned closer to end 34 than end 32. Osteograft 30 does not include any recesses 60 in top surfaces 44 adjacent end 34 or any recesses 60 in bottom surface adjacent end 32 such that recesses 60 in top surface 44 are not coaxial with recesses 60 in bottom surface 46 (FIGS. 11C and 11D). It is envisioned that recesses 60 in top and bottom surfaces 44, 46 may alternatively be positioned such that recesses 60 in top surface 44 are positioned closer to end 34 than end 32 and recesses 60 in bottom surface 46 positioned closer to end 32 than end 34. This configuration allows for a plug 62 comprising a material, such as, for example, demineralized bone inserted into recesses 60 to distribute osteoconductive and/or osteoinductive material from top surface 44 in one direction and a plug 62 to distribute osteoconductive and/or osteoinductive material from bottom surface 46 in an opposite direction.

In some embodiments, recesses 60 comprise about less than 50% of the entire graft 10. In some embodiments, recesses 60 comprise about less than 33% of the entire graft. In some embodiments, recesses 60 comprise about less than 66% of the entire graft. In some embodiments, recesses 60 comprise about less than 75% of the entire graft.

Figure 12A:
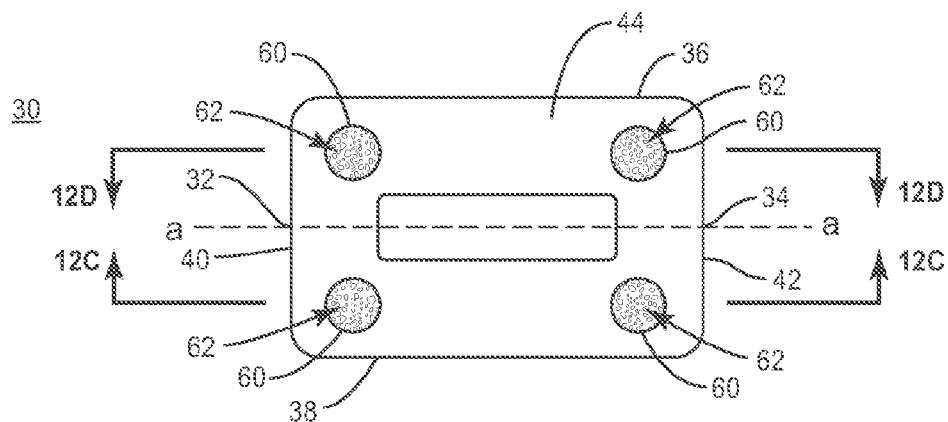
FIG. 12A illustrates a top view of one embodiment of an osteograft in accordance with the principles of the present disclosure.
Figure 12B:
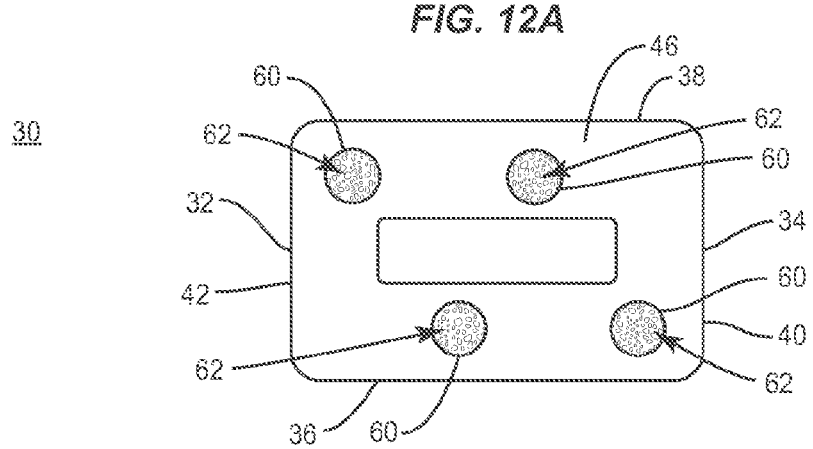
FIG. 12B illustrates a bottom view of the osteograft shown in FIG. 12A.
Figure 12C:
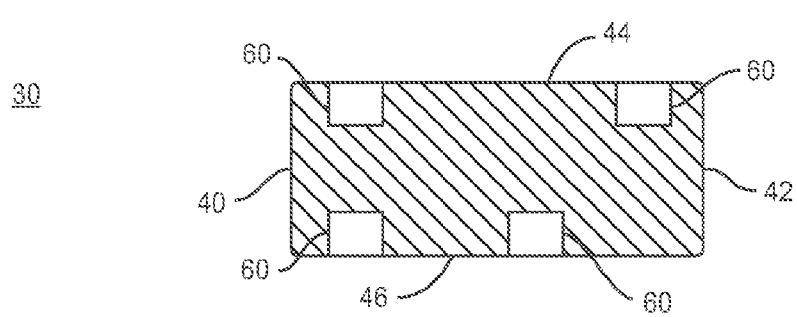
FIG. 12C illustrates a side cross sectional view of the osteograft shown in FIG. 12A.
Figure 12D:
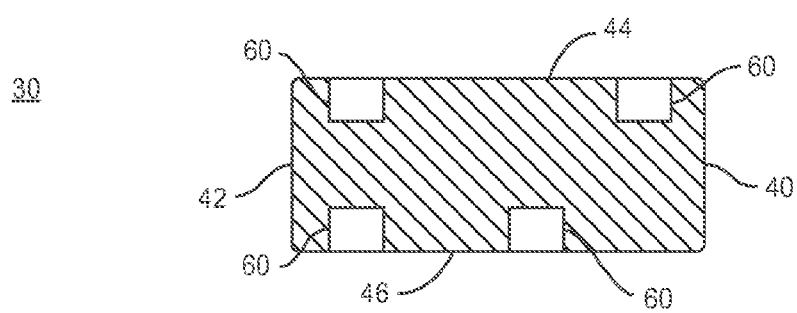
FIG. 12D illustrates a side cross sectional view of the osteograft shown in FIG. 12A.

It is envisioned that top and bottom surfaces 44, 46 of osteograft 30 may include any combination of the configurations of plugs 62 and recesses 60 shown in FIGS. 1A-11D. For example, top surface 44 may include at least one recess 60 in corners of top surface 44 between side wall 36 and end wall 40, between side wall 36 and end wall 42, between side wall 38 and end wall 40 and between side wall 38 and end wall 42 (FIG. 12A) and bottom surface 46 may include at least one recess 60 in corners of bottom surface 46 between side wall 36 and end wall 40 and between side wall 38 and end wall 42 (FIG. 12B). Bottom surface 46 also includes at least one recess 60 that is parallel with the recess(es) 60 in corner of bottom surface 46 between side wall 36 and end wall 40 along axis a and at least one recess 60 that is parallel with the recess(es) 60 in corner of bottom surface 46 between side wall 38 and end wall 42 along axis a (FIG. 12B) such that at least one recess 60 in top surface 44 is aligned with at least one recess 60 in bottom surface 46 and at least one recess 60 in top surface 44 is offset from at least one recess 60 in bottom surface 46 (FIGS. 12C and 12D). This allows a medical practitioner to vary the number of recesses 60 in osteograft 30 as well as determine suitable locations for such recesses 60 so that plugs 62 can be disposed therein to selectively deliver osteoinductive and/or osteoconductive material directly to specific areas of a patient's anatomy, depending upon the requirements of a particular application, without delivering osteoinductive and/or osteoconductive material directly to other areas.

Figure 13A:
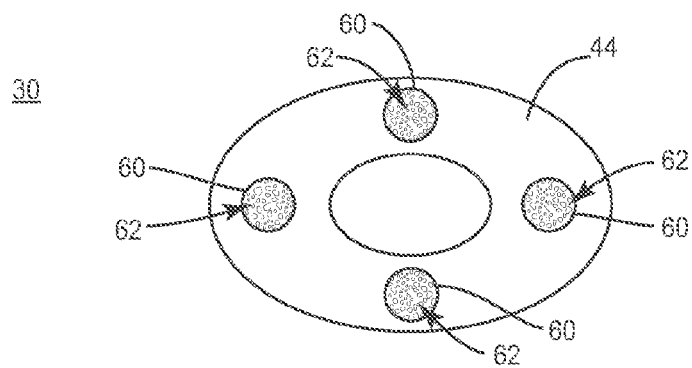
FIG. 13A illustrates a top view of one embodiment of an osteograft in accordance with the principles of the present disclosure.
Figure 13B:
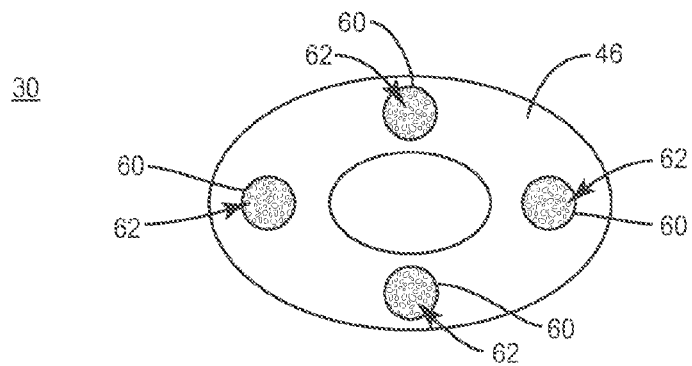
FIG. 13B illustrates a bottom view of the osteograft shown in FIG. 13A.
Figure 13C:
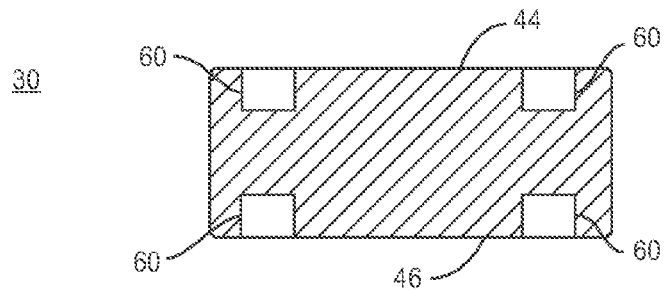
FIG. 13C illustrates a side cross sectional view of the osteograft shown in FIG. 13A.
Figure 13D:
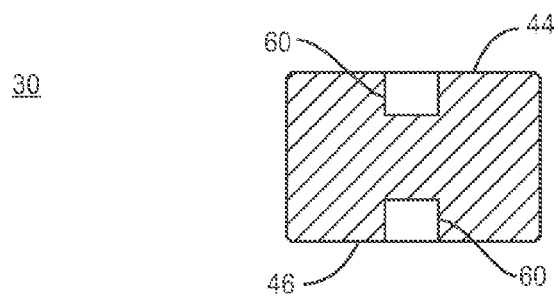
FIG. 13D illustrates a side cross sectional view of the osteograft shown in FIG. 13A.

In some embodiments, the body of osteograft 30 has a substantially oval cross sectional configuration (FIGS. 13A-13D). Osteograft 30 includes a plurality of recesses 60 that are distributed uniformly and circumferentially on top surface 44 (FIG. 13A) and bottom surface 46 (FIG. 13B) such that recesses 60 in top surface 44 are coaxial with recesses 60 in bottom surface 46 (FIGS. 13C and 13D). It is envisioned that top surface 44 may include one or a plurality of recesses 60 that are each coaxial with an equal number of recesses 60 in bottom surface 46. This configuration allows for a plug 62 comprising a material, such as, for example, demineralized bone inserted into recesses 60 to simultaneously distribute osteoconductive and/or osteoinductive material in the same amount and manner from top surface 44 as bottom surface 46.

In some embodiments, osteograft 30 is configured to increase the surface area contact of osteograft 30 with the host bone, which will result in faster fusion and incorporation of the osteograft 30 into host bone and ultimately a stronger fusion mass. In some embodiments, the allograft bone used to form osteograft 30 is surface demineralized to increase its osteoinductivity and fusion with the host bone.

In some embodiments, osteograft 30 comprises a plurality of pores extending into an outer surface thereof. In some embodiments, the pores in osteograft 30 are interconnected. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, osteograft 30 has a porosity of at least about 30%, at least about 50%, at least about 60%, at least about 70%, at least about 90%. The pores may support ingrowth of cells, formation or remodeling of bone, cartilage and/or vascular tissue.

In some embodiments, osteograft 30 may be seeded with harvested bone cells and/or bone tissue, such as for example, cortical bone, autogenous bone, allogenic bones and/or xenogenic bone. In some embodiments, osteograft 30 may be seeded with harvested cartilage cells and/or cartilage tissue (e.g., autogenous, allogenic, and/or xenogenic cartilage tissue). For example, before insertion into the target tissue site, osteograft 30 can be wetted with the graft bone tissue/cells, usually with bone tissue/cells aspirated from the patient, at a ratio of about 3:1, 2:1, 1:1, 1:3 or 1:2 by volume.

The bone tissue/cells are permitted to soak into the allograft provided, and the allograft may be kneaded by hand, thereby obtaining a pliable consistency that may subsequently be packed into the osteochondral defect.

In some embodiments, a therapeutic agent may be disposed on or in osteograft 30 by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in osteograft 30.

In some embodiments, recesses 60 can be drilled into osteograft 30 and then plug 62 implanted into the recess 60. In some embodiments, plugs 60 stay in recesses 60 better if plugs 62 are cored from freeze dried demineralized bone and then press-fit rather than coring undemineralized or fully mineralized bone plugs or inserts, demineralizing them, press-fitting into recesses 60 and freeze drying the complete osteograft 30, including plugs 62. Freeze drying causes plugs 62 to shrink and fall out of recesses 60. In some embodiments, plugs 62 are flush with an outer surface of osteograft 30 when disposed in recesses 60. In some embodiments, plugs protrude from osteograft 30 when disposed in recesses 60. In some embodiments, plugs are not flush with osteograft 30 when disposed in recesses 60, but are below its surface.

Osteograft 30 may also include mechanisms or features for reducing and/or preventing slippage or migration of the device during insertion. For example, one or more surfaces of osteograft 30 may include projections such as ridges or teeth (not shown) for increasing the friction between osteograft 30 and the adjacent contacting surfaces of the bone so to prevent movement of osteograft 30 after introduction to a desired location.

Growth Factors

In some embodiments, a growth factor and/or therapeutic agent may be disposed on or in osteograft 30 by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in osteograft 30 by the surgeon before osteograft 30 is administered or it may be available from the manufacturer beforehand.

Osteograft 30 may comprise at least one growth factor. These growth factors include osteoinductive agents (e.g., agents that cause new bone growth in an area where there was none) and/or osteoconductive agents (e.g., agents that cause in growth of cells into and/or through the allograft). Osteoinductive agents can be polypeptides or polynucleotides compositions. Polynucleotide compositions of the osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art, (See, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Preferred embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within a carrier are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta genes ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), TP508 (an angiogenic tissue repair peptide), as well as mixtures or combinations thereof.

In another embodiment, the one or more isolated osteoinductive agents useful in the bioactive formulation are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and or combination thereof; Osteoprotegerin; TGF-beta-1, TGF-beta-2, TGF-beta-3, or any combination thereof; or any combination of one or more members of these groups.

The concentrations of growth factor can be varied based on the desired length or degree of osteogenic effects desired. Similarly, one of skill in the art will understand that the duration of sustained release of the growth factor can be modified by the manipulation of the compositions comprising the sustained release formulation, such as for example, modifying the percent of allograft found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that simulate the natural healing process.

In some embodiments, a statin may be used as the growth factor. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfate, sodium thiosulfate, thimerosal, methylparaben, polyvinyl alcohol and phenylethyl alcohol; solubility adjusting agents; stabilizers;

and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

The amount of growth factor, e.g., bone morphogenic protein may be sufficient to cause bone and/or cartilage growth. In some embodiments, the growth factor is rhBMP-2 and is contained in one or more carriers in an amount of from 0.05 to 2 mg per cubic centimeter of the biodegradable carrier. In some embodiments, the amount of rhBMP-2 morphogenic protein is from 2.0 to 2.5 mg per cubic centimeter (cc) of the biodegradable carrier.

In some embodiments, the growth factor is supplied in an aqueous buffered solution. Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

In some embodiments, the BMP-2 is provided in a vehicle (including a buffer) containing sucrose, glycine, L-glutamic acid, sodium chloride, and/or polysorbate 80.

Additional Therapeutic Agents

The growth factors of the present application may be disposed on or in osteograft 30 with other therapeutic agents. For example, the growth factor may be disposed on or in osteograft 30 by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

Kits

In various embodiments, a kit is provided that includes osteograft 30 in a first compartment. A second compartment may include a plurality of plugs 62 comprising demineralized bone and having a polygonal cross-sectional configuration configured for disposal in one of recesses 60 and a plurality of plugs 62 comprising demineralized bone and having a circular cross-sectional configuration configured for disposal in one of recesses 60. A third compartment may include a biodegradable carrier and the growth factor and any other instruments needed for the implanting osteograft 30. A fourth compartment may include gloves, drapes, wound dressings and other procedural supplies for maintaining sterility during the implanting process, as well as an instruction booklet. A fifth compartment may include additional tools for implantation (e.g., drills, drill bits, bores, punches, etc.). Each tool may be separately packaged in a plastic pouch that is radiation sterilized. A sixth compartment may comprise an agent for radiographic imaging or the agent may be disposed on the allograft and/or carrier to monitor placement and tissue growth. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A kit comprising: an osteograft having a body comprising cortical bone extending between a first end and a second end along an axis and including an outer surface configured to engage host bone of a patient, the body including upper and lower surfaces and an inner surface defining a passage extending through the upper and the lower surface, the passage comprising two parallel side walls and two parallel end walls, the upper and lower surfaces each comprising a plurality of recesses extending transverse to the axis into the outer surface, the inner surface comprising a plurality of recesses extending parallel to the axis into the inner surface, the recesses each having a circular cross-sectional configuration; a plurality of plugs comprising demineralized bone and having a polygonal cross-sectional configuration configured for disposal in one of the recesses; and/or a plurality of plugs comprising demineralized bone and having a circular cross-sectional configuration configured for disposal in one of the recesses, wherein the two parallel side walls of the passage each comprise the plurality of recesses extending parallel to the axis.

2. A kit as recited in claim 1, wherein the recesses are uniform and each have a maximum width that is greater than a maximum with of the plugs having a circular cross-sectional configuration, the maximum width of the recesses being less than a maximum width of the plugs having a polygonal cross-sectional configuration.

\* \* \* \* \*

UNITED STATES PATENT AND TRADEMARK OFFICE
CERTIFICATE OF CORRECTION

PATENT NO. : 9,949,832 B2  
APPLICATION NO. : 15/048170  
DATED : April 24, 2018  
INVENTOR(S) : McKay Page 1 of 1

It is certified that error appears in the above-identified patent and that said Letters Patent is hereby corrected as shown below:

In the Specification

In Column 1, Line 5, delete "IMPLANT"." and insert -- IMPLANT", now Pat. No. 9,265,609. --, therefor.

In Column 6, Line 3, delete ""A" and insert -- A --, therefor.

In Column 13, Line 62, delete "plugs 60" and insert -- plugs 62 --, therefor.

In Column 20, Line 14, delete "plugs 60" and insert -- plugs 62 --, therefor.

In Column 24, Line 23, delete "and or" and insert -- and/or --, therefor.

In Column 24, Line 65, delete "sodium bisulfate, sodium bisulfate," and insert -- sodium bisulfate, sodium bisulfite, --, therefor.

In the Claims

In Column 27, Line 8, in Claim 2, delete "with" and insert -- width --, therefor.

Signed and Sealed this  
Fourteenth Day of August, 2018

Andrei Iancu  
*Director of the United States Patent and Trademark Office*